(12) United States Patent
Koo et al.

(10) Patent No.: US 6,747,166 B2
(45) Date of Patent: Jun. 8, 2004

(54) PROCESS FOR PREPARING CAROTENOID POLYENE CHAIN COMPOUNDS AND INTERMEDIATES FOR PREPARING THE SAME

(75) Inventors: Sangho Koo, 7-702, Sun-Kyung Apt., 506 Daechi-dong, Kangnam-ku, Seoul 135-280 (KR); Minkoo Ji, Seoul (KR)

(73) Assignees: Sangho Koo, Seoul (KR); SK Corporation, Seoul (KR)

( * ) Notice: Subject to any disclaimer, the term of this patent is extended or adjusted under 35 U.S.C. 154(b) by 34 days.

(21) Appl. No.: 10/220,697

(22) PCT Filed: Nov. 29, 2000

(86) PCT No.: PCT/KR00/01375

§ 371 (c)(1), (2), (4) Date: Aug. 30, 2002

(87) PCT Pub. No.: WO01/64630

PCT Pub. Date: Sep. 7, 2001

(65) Prior Publication Data

US 2003/0100785 A1 May 29, 2003

(30) Foreign Application Priority Data

Mar. 2, 2000 (KR) ......................................... 2000-10376

(51) Int. Cl.⁷ ............................................. C07C 303/00
(52) U.S. Cl. ........................................... 558/51; 558/44
(58) Field of Search ...................................... 558/51, 44

(56) References Cited

U.S. PATENT DOCUMENTS 3,850,991 A * 11/1974 Chabardes et al.
4,883,887 A * 11/1989 Bernhard et al.

* cited by examiner

Primary Examiner—Paul J. Killos
(74) Attorney, Agent, or Firm—Abelman, Frayne & Schwab

(57) ABSTRACT

The present invention provides an intermediate compound used for synthesis of polyene chain structure, that is an important moiety of carotenoid compounds, a process for preparing the same, and carotenoid polyene chain compounds prepared by using the intermediate, and, in particular, a process for preparing lycopene. The process for preparing the carotenoid polyene chain compound employs an allylic sulfone compound as starting material, which is reacted with C-5 sulfide compound to extend the carbon chain. The resultant thio-sulfone compound is oxidized, and the obtained disulfone compound is combined with C-10 di(haloallylic) sulfide compound to form a chain compound containing the desired number of carbon atoms. Then, the diallylic sulfone obtained by oxidation of the diallylic sulfide is subjected to Ramberg-Baklund reaction in order to form the central triene bond. After removal of sulfonyl groups, carotenoid polyene chain compound is obtained.

18 Claims, No Drawings

PROCESS FOR PREPARING CAROTENOID POLYENE CHAIN COMPOUNDS AND INTERMEDIATES FOR PREPARING THE SAME

TECHNICAL FIELD

The present invention relates to a process for preparing carotenoid polyene chain compounds. More specifically, it relates to intermediate compounds which are useful for synthesis of carotenoid compounds having polyene chain structure, and a process for preparing the same, and a process for preparing polyene chain compounds, especially lycopene, by using the intermediate compound.

BACKGROUND ART

Carotenoid compounds have polyene chain structure. Specific examples of the compounds include beta-carotene, lycopene, astaxanthin, bixin, and the like. The carotenoid compounds have been widely used as natural dyes, and recently, these compounds are reported to have excellent anti-tumor effect, by virtue of their selective reactivity with radicals and singlet oxygen known as carcinogens. In these circumstances, a variety of commercial products containing carotene, including cosmetics or taste food, have been merchandised. However, there still remain conflict opinions on the anti-tumor activity of beta-carotene, since beta-carotene is reported to have a harmful effect on smokers or patients having lung cancer. Thus, people pay more increasing attention to lycopene, having stronger anti-oxidation ability with no conflict opinion on the anti-tumor activity.

To meet such a tendency, the requirement of developing a process for effectively synthesizing polyene chain structures that construct lycopene also increases.

In the meanwhile, the most representative conventional synthetic process for preparing lycopene was developed by Isler; that is a process for synthesizing polyene chain on the basis of Wittig reaction (Reaction Scheme 1; *Helv. Chim. Acta* 1956, 39, 463–473).

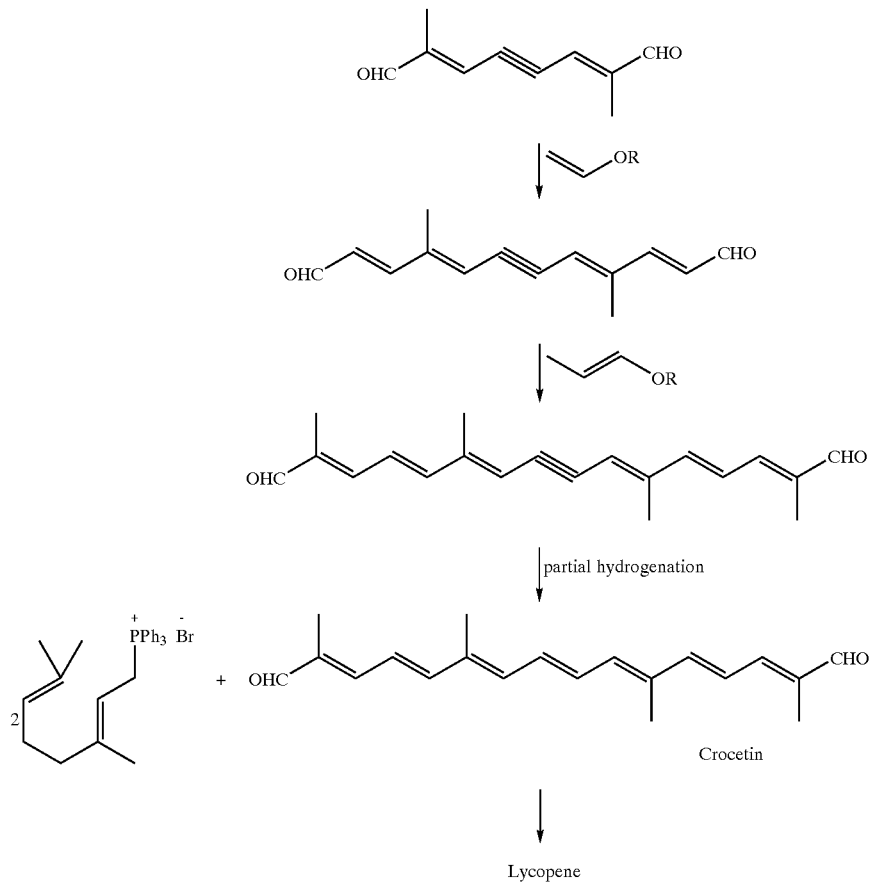

Reaction Scheme 1

According to Reaction Scheme 1, C-10 dialdehyde compound is subsequently reacted with vinyl ether and propenyl ether compound to form a continuously conjugated carbon chain wherein each C-2 unit and C-3 unit was respectively added to the aldehyde groups of C-10 dialdehyde compound. Throughout the stage, C-10 unit has been added to the dialdehyde to form C-20 dialdehyde, of which the triple bond at the center of the molecule was then partially reduced to give crocetin.

Then, crocetin thus obtained is subjected to Wittig Reaction with Wittig salts to form lycopene. The Wittig salts used in this stage is what was prepared as a result of reaction of geranyl bromide with triphenylphosphine.

However, the synthetic process for lycopene according to Reaction Scheme 1 includes many reaction stages to carry out in order to form crocetin, and the synthetic efficiency is low owing to the trouble in treating phosphine oxide as the by-product obtained as a result of Wittig Reaction.

Another synthetic process for synthesizing lycopene is developed by Karrer. The process is based on coupling reaction by using alkynyl anion, partial hydrogenation and dehydration. The synthetic process is illustrated in Reaction Scheme 2 (*Helv. chim. Acta* 1950, 33, 1349–1352).

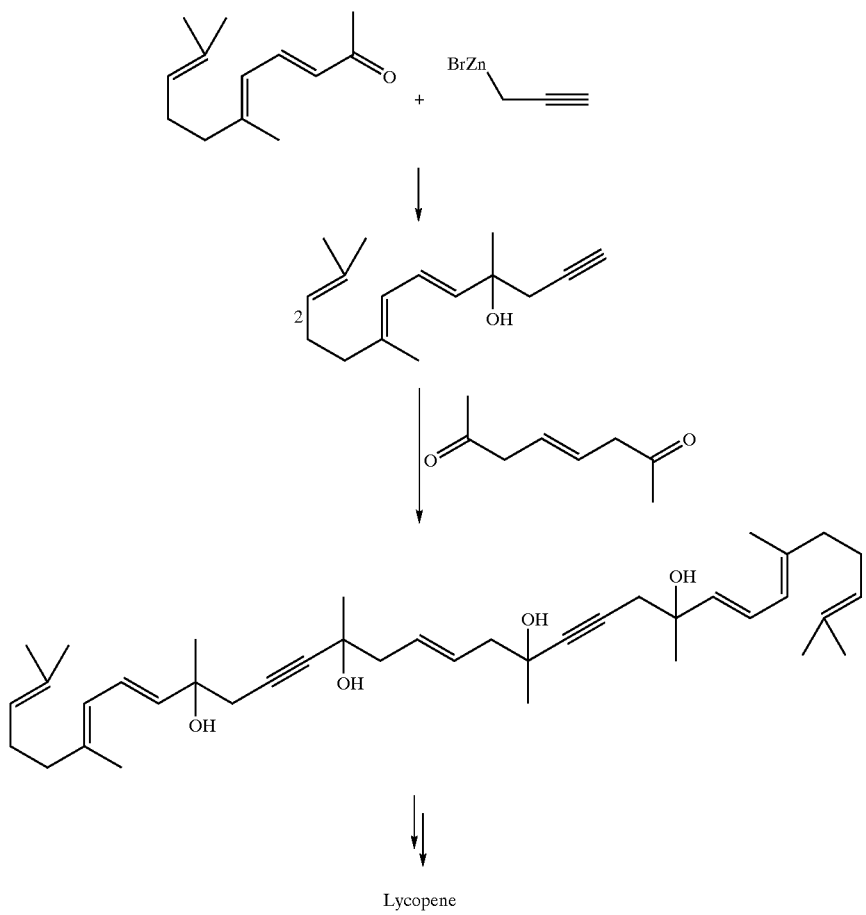

Reaction Scheme 2

According to Reaction Scheme 2, an anion obtained by adding metallic zinc to propargylic bromide is subjected to coupling reaction with ψ-ionone, to give C-16 intermediate. Then, two molecules of the alkynyl anion obtained by adding bases to the C-16 intermediate were coupled with C-8 diketone compound to form forwards containing 40 carbon atoms required for synthesis of lycopene. The partial hydrogenation of the two triple bonds and dehydration of the forward compound provide lycopene.

The synthetic process for lycopene according to Reaction Scheme 2 is relatively simple, however, it is not easy to form a double bond having trans configuration.

Thus, the first technical object of the present invention is to provide an allylic sulfide, that is, a C-5 compound usable for chain extension to effectively synthesize polyene chain structure described above.

Another technical object of the present invention is to provide a process for extending the carbon chain by the use of said allylic sulfide.

Still another object of the present invention is to provide a process for preparing polyene chain compounds, especially lycopene, by using said process for extending carbon chain.

DISCLOSURE OF THE INVENTION

In order to achieve the first technical object, the present invention provides allylic sulfides represented by Chemical Formula 1:

Chemical Formula 1

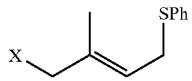

Wherein, X is selected from the group consisting of —Cl, —Br, —I, —OSO$_2$CF$_3$, —OSO$_2$Ph, —OSO$_2$C$_6$H$_4$CH$_3$ and —OSO$_2$CH$_3$, and Ph represents phenyl group.

The second technical object of the present invention is achieved by a process for preparing an allylic sulfide of Chemical Formula 1, which comprises the steps of (a-1) oxidizing isoprene to obtain isoprene monoxide, (b-1) reacting the isoprene monoxide with benzene thiol to obtain 4-hydroxy-3-methyl-2-butenyl phenyl sulfide (A); and (c-1)

reacting the compound (A) with a halogenating compound or sulfonylating compound.

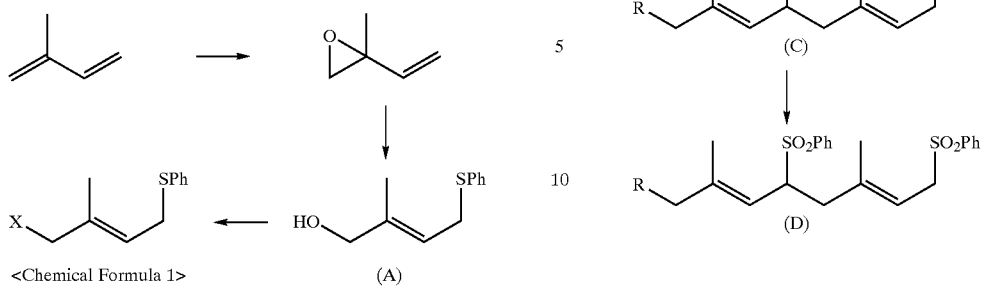

In the formulas, X is selected from the group consisting of —Cl, —Br, —I, —OSO$_2$CF$_3$, —OSO$_2$Ph, —OSO$_2$C$_6$H$_4$CH$_3$ and —OSO$_2$CH$_3$, and Ph represents phenyl group.

The third technical object of the present invention is achieved by a process for extending carbon chain by the use of allylic sulfide of Chemical Formula 1, which comprises the steps of (a-2) deprotonating allylic sulfone compound (B), and reacting the resultant compound with allylic sulfide of Chemical Formula 1 to obtain thio-sulfone compound (C); and (b-2) selectively oxidizing the thio-sulfone compound (C) to obtain the corresponding allylic sulfone compound (D).

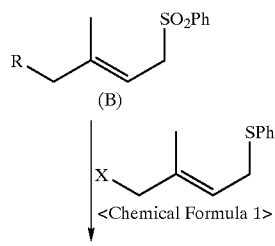

In the formulas, R is selected from the group consisting of hydrogen, C1~C30 alkyl group, C1~C30 alkenyl group, aryl group, —CN, —COOR' (wherein, R' is C1~C10 alkyl group) and —C(=O)H, X is selected from the group consisting of —Cl, —Br, —I, —OSO$_2$CF$_3$, —OSO$_2$Ph, —OSO$_2$C$_6$H$_4$CH$_3$ and —OSO$_2$CH$_3$, and Ph represents phenyl group.

The fourth technical object of the present invention is achieved by a process for preparing a carotenoid polyene chain compound represented by Chemical formula 2, which comprises the steps of (a-3) deprotonating the allylic disulfone compound (D), and reacting the resultant compound with not more than 0.5 equivalent of diallylic sulfide (E) (wherein, Y is a halogen atom) on the basis of 1 equivalent of allylic disulfone compound (D) to obtain allylic sulfide compound (F); (b-3) selectively oxidizing the allylic sulfide compound (F) to obtain allylic sulfone compound (G); (c-3) subjecting the allylic sulfone compound (G) to Ramberg-Baklund reaction to give tetra(phenylsulfonyl)-triene compound (H); and (d-3) reacting the compound (H) with a base. If R of Chemical Formula 2 is prenyl, the process provides lycopene.

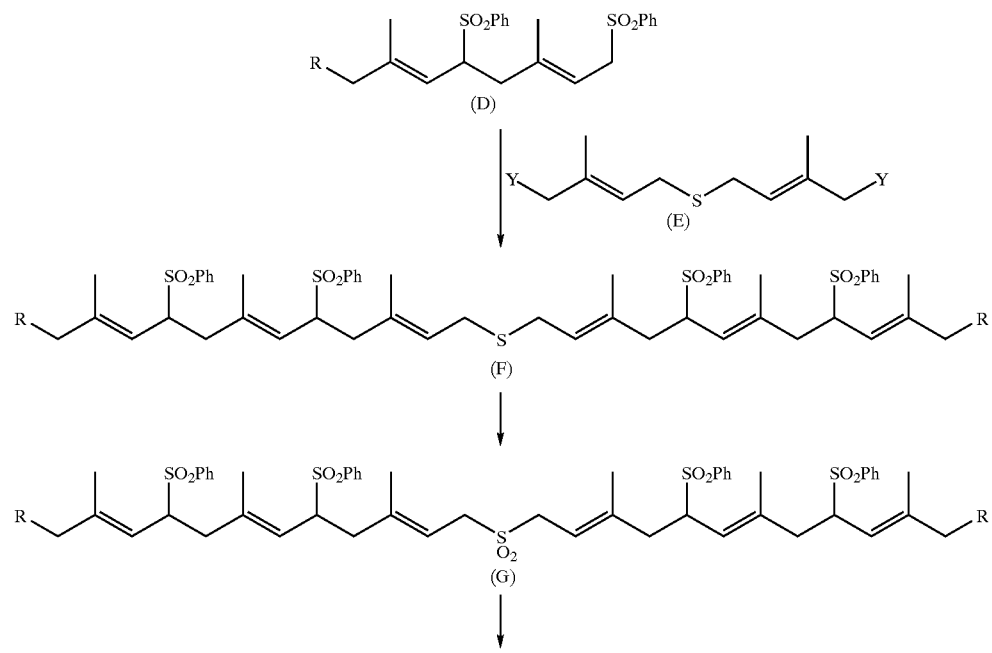

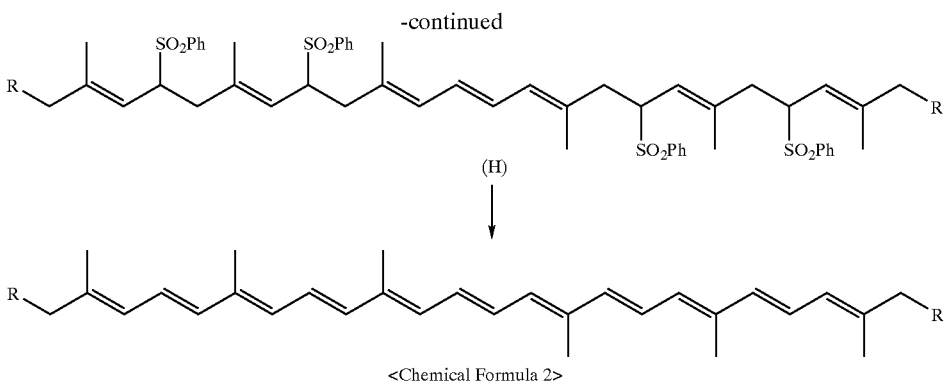

<Chemical Formula 2>

In the formulas, R is selected from the group consisting of hydrogen, C1~C30 alkyl group, C1~C30 alkenyl group, aryl group, —CN, —COOR' (wherein, R' is C1~C10 alkyl group) and —C(=O)H, Y is selected from the group consisting of —Cl, —Br, —I, —OSO$_2$CF$_3$, —OSO$_2$Ph, —OSO$_2$C$_6$H$_4$CH$_3$ and —OSO$_2$CH$_3$, and Ph represents phenyl group.

In the process for preparing an allylic sulfide of Chemical Formula 1, the ring opening of isoprene monoxide of stage (b-1) is preferably performed by using Cu(I)-containing salt as a catalyst, and N,N-dimethylformamide (DMF) as solvent, because the objective compound having a double bond of trans configuration can be obtained as major product under such reaction conditions.

In the process for extending carbon chain by the use of allylic sulfide of Chemical Formula 1, specific examples of R include methyl, ethyl and propyl group for C1~C30 alkyl group, vinyl, allyl and prenyl group for C1~C30 alkenyl group, and phenyl and naphthyl group for aryl group. X is preferably Cl or Br in terms of reactivity, while R is preferably hydrogen or prenyl.

Further, the C-5 unit can be added as desired by repeating stage (a-2) and (b-2) one or more times by using compound (D) as the starting material.

Selective oxidation of stage (b-2) can be preferably performed by adding hydrogen peroxide solution dropwise to thio-sulfone compound (C) in the presence of a metal oxide catalyst such as lithium molybdenate-niobate (LiNbMoO$_6$) or vanadium oxide (V$_2$O$_5$) at room temperature. Selective oxidation under such reaction conditions gives excellent yields.

In the process for preparing a carotenoid polyene chain compound represented by Chemical formula 2, specific examples of R include methyl, ethyl and propyl group for C1~C30 alkyl group, vinyl, allyl and prenyl group for C1~C30 alkenyl group, and phenyl and naphthyl group for aryl group. In particular, it is preferable that R is hydrogen or prenyl.

In the stage (a-3), Y of compound (E) is preferably Br in terms of reactivity, if R of allylic disulfone compound (D) is hydrogen or prenyl. Deprotonation of allylic disulfone compound (D) should be performed by adding 2 equivalent of base to 1 equivalent of allylic disulfone compound (D) at low temperature, preferably at a temperature not higher than −40° C. Specific examples of the base include n-BuLi, s-BuLi, t-BuLi, phenyl lithium, NaNH$_2$, lithium diisopropylamide (LDA), lithium hexamethyldisilazide, sodium hexamethyldisilazide, and the like.

Selective oxidation of stage (b-3) can be preferably performed by adding a mixture of urea-hydrogen peroxide (UHP) and phthalic anhydride dropwise to allylic disulfone compound (D) at low temperature, or adding hydrogen peroxide solution dropwise to sulfide compound (D) in the presence of a metal oxide catalyst such as lithium molybdenate-niobate (LiNbMoO$_6$) or vanadium oxide (V$_2$O$_5$) at room temperature.

Ramberg-Baklund reaction of stage (c-3) is preferably carried out under a condition excluding oxygen in the air, for example, under nitrogen or argon atmosphere in terms of reactivity and yield.

The base used in stage (d-3) is not particularly restricted. Specific examples include NaNH$_2$/NH$_3$, and metal alkoxides such as CH$_3$OK/CH$_3$OH, CH$_3$ONa/CH$_3$OH, CH$_3$CH$_2$OK/CH$_3$CH$_2$OH, CH$_3$CH$_2$ONa/CH$_3$CH$_2$OH and t-BuOK/t-BuOH. Among them, metal alkoxide is more preferably used as the base.

The allylic sulfide of Chemical Formula 1 according to the present invention, which can be used as a ground material for chain extension due to the bonding with allylic sulfone compound in the course of synthesizing a polyene chain containing compound, is synthesized as described below:

Firstly, isoprene is oxidized to give isoprene monoxide. Though the oxidation reaction may be carried out under a conventional oxidative reaction condition, the present invention employs the condition of using an oxidant such as m-chloroperoxybenzoic acid (MCPBA), or of forming a corresponding halohydrin from isoprene (J. Am. Chem. Soc., 1950, 72, 4608–4613) which is then reacted with a base. Among them, the latter is more preferable as considering regio-selectivity of the two double bonds of isoprene on the electrophilic reactant.

Then, the isoprene monoxide is reacted with benzene thiol (PhSH) to provide 4-hydroxy-3-methyl-2-butenyl phenyl sulfide (A). In the reaction, it is preferable to employ Cu(I)-containing salt as a catalyst, and N,N-dimethylformamide as solvent in the aspect of reactivity and yield. Under these reaction conditions, the reactivity is high so that the reaction can be performed under mild condition at ambient temperature, and the reaction process itself is simple and easy to provide economic and practical advantages. The yield is also good. As the Cu(I)-containing salt, any salt having Cu$^+$ ion is usable, but CuCN, CuBr, CuI or CuCl is preferably used. The Cu(I)-containing salt is used in a catalytic amount, more specifically, 0.001~0.1 mol % of the salt is preferably used on the basis of 1 mole of isoprene monoxide.

As a result of the above reaction, ring opening at the allylic position of the epoxide compound is performed. In the 4-hydroxy-3-methyl-2-butenyl phenyl sulfide (A) molecules thus obtained, trans configuration prevails in a trans:cis ratio of 6:1 or more.

Thereafter, 4-hydroxy-3-methyl-2-butenyl phenyl sulfide (A) is subjected to halogenation or sulfonylation to provide allylic sulfide of Chemical Formula 1. In this stage, halogenation of 4-hydroxy-3-methyl-2-butenyl phenyl sulfide (A) may be carried out under various reaction conditions. For example, halogenation can be performed by employing a reaction condition of $CH_3SO_2Cl/LiCl$, $SOCl_2$, $(COCl)_2$, $PPh_3/CCl_4$, HCl, $PBr_3$, $PPh_3/NBS$ or HBr. Sulfonylation may be carried out under various conditions as well, for example under the condition of using a sulfonyl compound such as $CF_3SO_2Cl$, $PhSO_2Cl$, $CH_3C_6H_4SO_2Cl$ and $CH_3SO_2Cl$ with a base such as triethylamine ($Et_3N$) and pyridine (Reaction Scheme 3).

Reaction Scheme 3

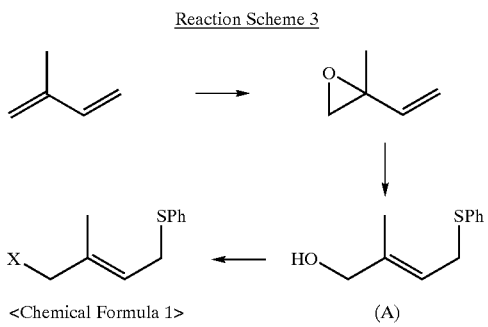

<Chemical Formula 1>     (A)

In the formulas, X is selected from the group consisting of —Cl, —Br, —I, —$OSO_2CF_3$, —$OSO_2Ph$, —$OSO_2C_6H_4CH_3$ and —$OSO_2CH_3$, preferably from —Cl and —Br.

Now, the reaction of ring opening at the allylic position of the isoprene monoxide is described in detail.

The ring opening reaction of isoprene monoxide may be carried out under the conditions other than the reaction condition used in the present invention. Specific reaction conditions and the product distribution under each condition are shown in Table 1 below. In Table 1, Entry 5 corresponds to the reaction by using Cu(I)-containing salt and benzenethiol according to the present invention, while Entries 1 to 3 to the reaction of isoprene monoxide under basic condition, and Entries 4 and 6 to the reaction under acidic condition. The ratios of cis:trans double bond in 4-hydroxy-3-methyl-2-butenyl phenyl sulfide (A) are determined by using gas chromatography and $^1$H-NMR.

TABLE 1

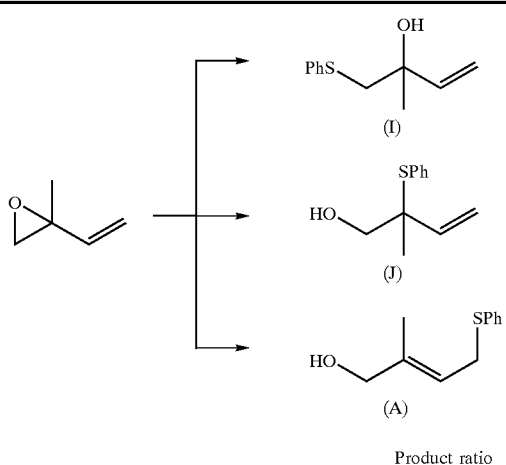

| Entry | Reaction Condition | Yield (%) | (I) | (J) | (A) (cis:trans) |
|---|---|---|---|---|---|
| 1 | $Et_3N$, PhSH in MeOH, 0° C.~room temperature, 6 Hr | 99 | 96 | 3 | 1 |
| 2 | NaH, PhSH in THF, 0° C.~room temperature, 6 Hr | 96 | 98 | — | 2 |
| 3 | n-BuLi, PhSH in THF, −78° C.~room temperature, 6 Hr | 100 | 100 | — | — |
| 4 | $LiClO_4$, PhSH in DMF, room temperature, 6 Hr | 44 | 60 | 18 | 22(1:4) |
| 5 | CuI(cat.), PhSH in DMF, room temperature, 6 Hr | 99 | — | 12 | 87(1:6) |
| 6 | $AlEt_3$, PhSH in benzene, room temperature, 6 Hr | 94 | — | 7 | 93(100:0) |
| 7 | $Pd(Ph_3)_4$(cat.), PhSH in THF, room temperature, 6 Hr | 3 | — | — | 100(1:9) |
| 8 | $Pd(OAc)_2/PPh_3$(cat.), PhSH in THF, room temperature, 6 Hr | 7 | — | — | 100(1:12) |

As shown in Table 1, in case of Entries 1 to 3, compound (I) was obtained as the main product, while the desired 4-hydroxy-3-methyl-2-butenyl phenyl sulfide (A) was not produced at all, or was produced in an extremely small amount. In case of Entry 4, 4-hydroxy-3-methyl-2-butenyl phenyl sulfide (A) was synthesized at a low yield of about 22%, and the cis:trans ratio showed relatively low trans product (1:4) as compared to Entry 5.

In case of Entry 6 (Tetrahedron Lett. 1981, 22, 2413–2416), the desired compound, 4-hydroxy-3-methyl-2-butenyl phenyl sulfide (A) could be obtained at a high yield of 93%, however, only to provide cis-configuration of compound (A). In case of Entries 7 and 8, 4-hydroxy-3-methyl-2-butenyl phenyl sulfide (A) of which trans configuration prevails could be obtained, however, the synthetic yield of 4-hydroxy-3-methyl-2-butenyl phenyl sulfide (A) was very low (3% and 7%, respectively).

On the contrary, in case of Entry 5, the reaction condition of the present invention, 4-hydroxy-3-methyl-2-butenyl phenyl sulfide (A) was obtained with an excellent yield of about 87%, and the trans configuration prevails with cis:trans ratio of 1:6 or less. As shown above, 4-hydroxy-3-methyl-2-butenyl phenyl sulfide (A) of which trans configuration of double bond prevails could be synthesized at a high yield under the reaction condition according to the present invention.

In the meanwhile, in order to synthesize the carotenoid polyene chain compounds of Chemical Formula 2, which is represented by lycopene, the allylic sulfone compound (D) having extended carbon chain as desired should be firstly synthesized. As referring to Reaction Scheme 4, the process for preparing di(allylic sulfone) compound (D) is described here-in-below:

After deprotonation of the starting material, allylic sulfone compound (B), by treating with base, allylic sulfide of Chemical Formula 1 is added thereto, to obtain thio-sulfone compound (C) with 5-carbon chain extended. The specific examples of the allylic sulfone compound (B) include geranyl sulfone (R=prenyl) and prenyl sulfone (R=hydrogen). As the base, n-butyl lithium (n-BuLi) is preferably used.

The chain extension may be carried out at ambient temperature, but more preferably at a low temperature of 0° C. or lower. In case of chain extension by using geranyl sulfone as the starting material, X of the compound of Chemical Formula 1 is preferably Br in terms of reactivity.

Then, the sulfide group of thio-sulfone compound (C) is selectively oxidized to provide the corresponding allylic disulfone compound (D). The selective oxidation is preferably carried out under the condition of employing metal oxide such as $LiNbMoO_6$ or $V_2O_5$ as a catalyst, and hydrogen peroxide ($H_2O_2$) as an oxidant.

Reaction Scheme 4

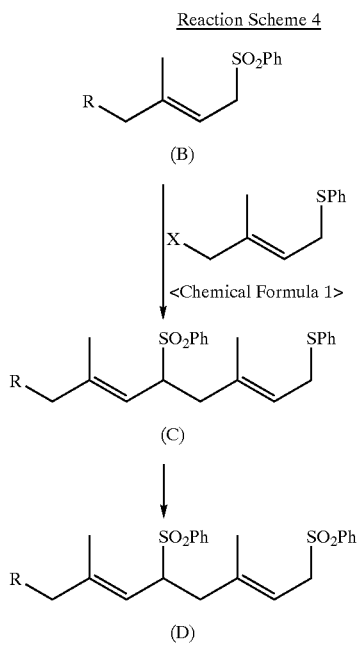

In the formulas, R is selected from the group consisting of hydrogen, C1~C30 alkyl group, C1~C30 alkenyl group, aryl group, —CN, —COOR' (wherein, R' is C1~C10 alkyl group) and —C(=O)H, X is selected from the group consisting of —Cl, —Br, —I, —$OSO_2CF_3$, —$OSO_2Ph$, —$OSO_2C_6H_4CH_3$ and —$OSO_2CH_3$.

When R is —CN, —COOR' (wherein, R' is $C_1C10$ alkyl group) or —C(=O)H, the corresponding compound can be prepared according to conventional processes to introduce such a functional group.

If the process for chain extension is repeated, novel allylic sulfone compounds with increased five carbon numbers can be obtained every time.

Now, the synthesis of carotenoid polyene chain compound represented by Chemical Formula 2 according to the present invention is described in detail (see Reaction Scheme 5). The process for preparing carotenoid polyene chain compound according to the present invention is based on the process for synthesizing beta-carotene developed by the present inventors (*J. Org. Chem.* 1999, 64, 8051–8053). It is characterized by using di(haloallylic) sulfide (E) in order to synthesize C-10 triene structure of the center of the polyene chain, and applying Ramberg-Bäklund reaction to diallylic sulfone obtained by oxidation of the sulfide compound.

In order to obtain the carbon skeletal required for carotenoids, di(haloallylic) sulfide (E) is combined with 2 equivalents or more of allylic disulfone compound (D) based on 1 equivalent of compound (E) by means of Julia method (*Bull. Soc. Chim.* Fr., 1973, 743–750), to obtain allylic sulfide (F). The coupling reaction of di(haloallylic) sulfide (E) with allylic disulfone compound (D) is preferably carried out by adding 2 equivalents of base such as n-BuLi to allylic disulfone compound (D) to deprotonate the compound, and then the reaction is performed under a temperature condition of −40° C. or lower. In di(haloallylic) sulfide (E), Y is preferably Br in terms of reactivity.

Then, only the sulfur of allylic sulfide (F) is selectively oxidized to give the corresponding sulfone compound (G). The selective oxidation reaction is preferably carried out by adding a mixture of UHP and phthalic anhydride dropwise to allylic sulfide compound (F) at a low temperature, or by adding $H_2O_2$ dropwise to the compound in the presence of $LiNbMoO_6$ or $V_2O_5$ as a catalyst at ambient temperature. Under such a reaction condition, only sulfur is selectively oxidized without oxidation of the double bond of allylic sulfide (F).

Thereafter, $SO_2$ at the center of the structure of sulfone compound (G) is removed to form a double bond to provide compound (H). This reaction is preferably performed by treating sulfone compound (G) under Ramberg-Bäklund reaction condition (*J. Am. Chem. Soc.*, 1969, 91, 7510–7512).

Lastly, four benzenesulfonyl groups are removed from compound (H) by heating the compound in the presence of alcohol solvent and alkoxide base such as sodium alkoxide, to synthesize the polyene chain compound of Chemical Formula 2 represented by lycopene.

Reaction Scheme 5

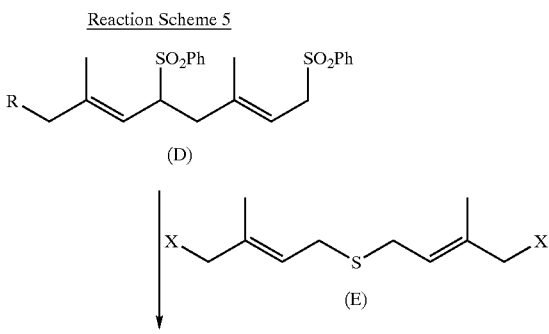

-continued

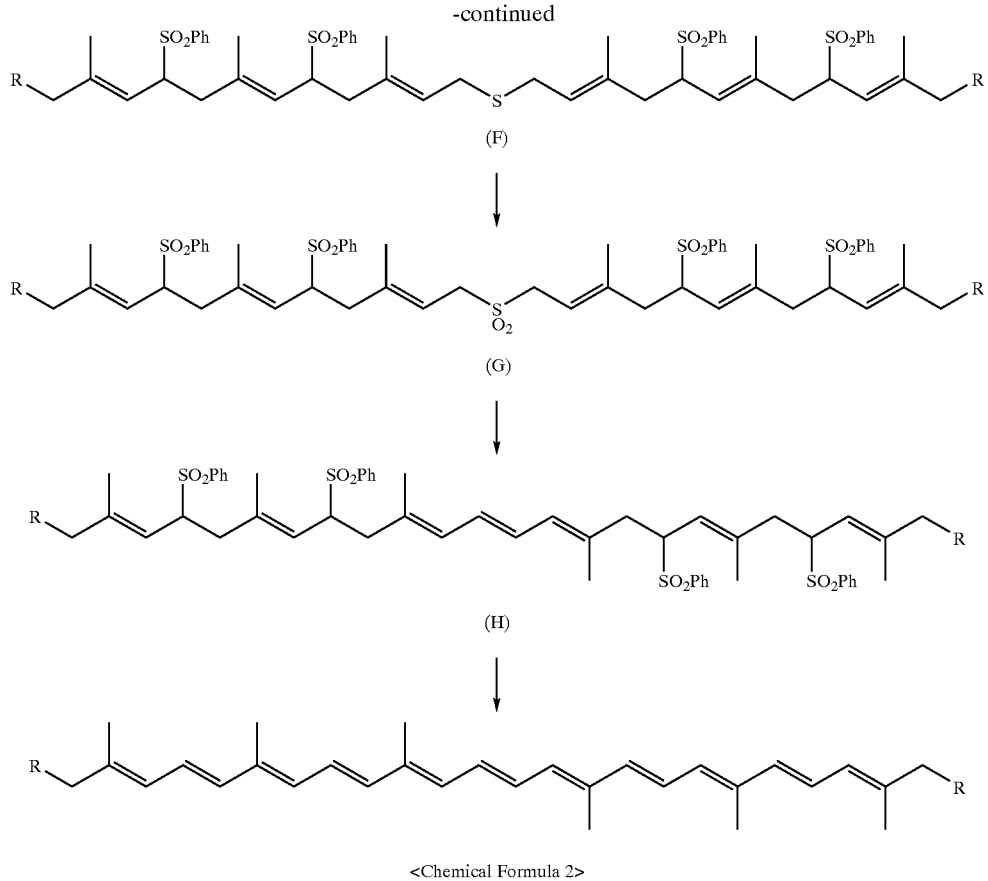

<Chemical Formula 2>

In the formulas, R is selected from the group consisting of hydrogen, C1~C30 alkyl group, C1~C30 alkenyl group, aryl group, —CN, —COOR' (wherein, R' is C1~C10 alkyl group) and —C(=O)H, X is selected from the group consisting of —Cl, —Br, —I, —OSO$_2$CF$_3$, —OSO$_2$Ph, —OSO$_2$C$_6$H$_4$CH$_3$ and —OSO$_2$CH$_3$.

When the carotenoid compounds represented by lycopene are prepared according to the present invention (Example 1 to 10), the synthetic process is simpler, easier and more efficient than conventional processes. In addition, the problem of treating byproducts such as phosphine oxide can be prevented according to the present invention. The process of the present invention is also advantageous in easily forming the polyene chain structure having trans configuration of double bond.

Allylic sulfide compound of Chemical Formula 1 according to the present invention is very useful for an intermediate compound to extend C5 chain, during the course of synthesis of polyene chain compound such as lycopene.

According to the present invention, a carotenoid polyene chain compound represented by lycopene of Chemical Formula 2 can be prepared by coupling of allylic sulfone compound (D) of the desired chain length and di(haloallylic) sulfide compound (E), and oxidizing the sulfide to give the corresponding diallylic sulfone compound, which is then subjected to Ramberg-Bäklund reaction, and finally eliminating the sulfonyl groups to give conjugated double bonds.

The invention is described in more detail by referring to the examples below, but it should be noticed that the present invention is not restricted to the examples by any means.

EXAMPLE 1

2-Methyl-4-phenylthio-2-buten-1-ol

Isoprene monoxide (0.30 ml, 3.1 mmol) was dissolved in N,N-dimethylformamide (DMF) (7 ml), and cuprous iodide (CuI) (15 mg, 0.08 mmol) and benzene thiol (PhSH) (0.33 ml, 3.2 mmol) were added thereto at 0° C. The resultant reaction mixture was stirred at the same temperature for about 6 hours.

When the reaction was completed, the reaction mixture was diluted with ether, washed with 1M-HCl three times (10 ml×3), dried over anhydrous sodium sulfate, and filtered. The filtrate was concentrated by evaporation under reduced pressure, and the residue was purified by silica gel column chromatography to obtain 2-methyl-4-phenylthio-2-butene-1-ol (0.52 g, 2.7 mmol) (yield: 87%). According to the analytical data of $^1$H-NMR and gas chromatography, the ratio of trans- to cis-double bond was not less than 6:1.

$^1$H-NMR: trans δ1.56 (s,3H), 2.38 (br s, 1H),3.55 (d, 2H, J=7.7 Hz), 3.92 (s, 2H), 5.54 (t, 1H, J=7.7 Hz), 7.15~7.35 (m, 5H); cis δ1.75 (s, 3H), 2.38 (br s, 1H), 3.52 (d, 2H, J=7.9 Hz), 3.90 (s, 2H), 5.41 (t, 1H, J=7.9 Hz), 7.15~7.35 (m, 5H). $^{13}$C-NMR: δ13.6, 31.5, 67.7, 119.9, 126.2, 128.9, 129.8, 136.3, 139.0. HRMS(EI) C$_{11}$H$_{14}$OS Calculated: 194.0765, Measured: 194.0771.

EXAMPLE 2

4-Bromo-3-methyl-2-butenyl phenyl sulfide

To a solution of 2-methyl-4-phenylthio-2-butene-1-ol (23.7 g, 122 mmol) dissolved in ether (80 ml), PBr$_3$ (16.5 g, 61 mmol) was slowly added at 0° C. The resultant reaction mixture was stirred at 0° C. for about 1 hour. When the reaction was completed, the reaction mixture was diluted with ether, washed with distilled water, dried over anhydrous sodium sulfate, and filtered. The filtrate was concentrated by evaporation under reduced pressure, and the residue was purified by silica gel column chromatography to obtain 4-bromo-3-methyl-2-butenyl sulfide (26.8 g, 104 mmol) (yield: 85%)

$^1$H-NMR: trans δ1.64 (s, 3H), 3.51 (d, 2H, J=7.7 Hz), 3.92 (s, 2H), 5.72 (t, 1H, J=7.7 Hz), 7.18~7.41 (m, 5H); cis δ 1.85 (s, 3H), 3.56 (d, 2H, J=7.9 Hz), 3.79 (s, 2H), 5.52 (t, 1H, J=7.9 Hz), 7.18~7.41 (m, 5H). $^{13}$C-NMR: δ14.7, 32.4, 40.4, 125.9, 126.7, 128.9, 130.9, 135.4, 135.5.

EXAMPLE 3-1

5-Phenylsulfonyl-1-phenylthio-3,7,11-trimethyl -2,6,10-dodecatriene

Geranyl sulfone (28.7 g, 103 mmol) was dissolved in THF (150 ml), and n-BuLi (1.6M solution in hexane/64 ml, 103 mmol) was slowly added thereto at 0° C. The resultant mixture was stirred for 20 minutes, and 4-bromo-3-methyl-2-butenyl phenyl sulfide (29.1 g, 113 mmol) was added to the reaction mixture. The reaction temperature was slowly raised to room temperature, and the mixture was stirred at the same temperature for about 11 hours.

To the reaction mixture, ether 100 ml was added, and the resultant mixture was subsequently washed with aqueous 1M-HCl solution (20 ml×2) and distilled water (30 ml). The mixture was dried over anhydrous sodium sulfate, and filtered.

The filtrate was concentrated by evaporation under reduced pressure, and the residue was purified by silica gel column chromatography to obtain 5-phenylsulfonyl-1-phenylthio-3,7,11-trimethyl-2,6,10-dodecatriene (43.6 g, 96 mmol) (yield: 93%).

$^1$H-NMR: δ1.13 (s, 3H), 1.53 (s, 3H), 1.59 (s, 3H), 1.68 (s, 3H), 1.92 (br s, 4H), 2.31 (dd, 1H, J=13.2, 11.4 Hz), 2.90 (dd, 1H, J=13.2, 3.0 Hz), 3.48 (d, 2H, J=7.5 Hz), 3.87 (ddd, 1H, J=11.4, 10.3, 3.0 Hz), 4.88 (d, 1H, J=10.3 Hz), 5.01 (br s, 1H), 5.32 (t, 1H, J=7.5 Hz), 7.15~7.38 (m, 5H), 7.40~7.58 (m, 2H), 7.58~7.70 (m, 1H), 7.75~7.90 (m, 2H). $^{13}$C-NMR: δ16.0, 16.4, 17.7, 25.7, 26.2, 31.8, 37.1, 39.6, 63.2, 116.8, 123.0, 123.6, 126.1, 128.7, 128.8, 129.3, 129.5, 131.9, 133.5, 134.6, 136.5, 137.6, 145.6.

EXAMPLE 3-2

5-Phenylsulfonyl-1-phenylthio-3,7-dimethyl -2,6-octadiene

Prenyl sulfone (20.2 g, 103 mmol) was dissolved in THE (100 ml), and n-BuLi (1.6M solution in hexane/72 ml, 115 mmol) was slowly added thereto at 0° C. The resultant mixture was stirred for 20 minutes, and 4-bromo-3-methyl-2-butenyl phenyl sulfide (25.9 g, 101 mmol) was added to the reaction mixture. The reaction temperature was slowly raised to room temperature, and the mixture was stirred at the same temperature for about 3 hours.

To the reaction mixture, ether 100 ml was added, and the resultant mixture was subsequently washed with aqueous 1M-HCl solution (20 ml×2) and distilled water (30 ml). The mixture was dried over anhydrous sodium sulfate, and filtered.

The filtrate was concentrated by evaporation under reduced pressure, and the residue was purified by silica gel column chromatography to obtain 5-phenylsulfonyl-1-phenylthio-3,7-dimethyl-2,6-octadiene (33.9 g, 87.7 mmol) (yield: 91%).

$^1$H-NMR: δ1.11 (s, 3H), 1.52(s, 3H), 1.61 (s, 3H), 2.31 (dd, 1H,J=13.6, 11.6 Hz), 2.86 (dd, 1H, J=13.6, 2.9 Hz), 3.48 (d, 2H, J=7.7 Hz), 3.84 (ddd, 1H, J=11.6, 10.4, 2.9 Hz), 4.86 (ddd, 1H, J=10.3, 1.4, 1.3 Hz), 5.31 (t, 1H, J=7.7 Hz), 7.15~7.30 (m, 5H), 7.48~7.53 (m, 2H), 7.59~7.61 (m, 1H), 7.80~7.82 (m, 2H). $^{13}$C-NMR: δ16.0, 17.9, 25.7, 31.8, 37.0, 63.3, 117.0, 123.1, 126.1, 128.7, 128.7, 129.2, 129.6, 133.4, 134.5, 136.4, 137.7, 145.1.

EXAMPLE 4-1

1,5-Di(phenylsulfonyl)-3,7,11-trimethyl-2,6,10-dodecatriene

In methyl alcohol (20 ml), dissolved was 5-phenylsulfonyl-1-phenylthio-3,7,11-trimethyl-2,6,10-dodecatriene (1.00 g, 2.2 mmol), and LiNbMoO$_6$ (32 mg, 0.11 mmol) and H$_2$O$_2$ (30% aqueous solution) (0.75 g, 6.6 mmol) were added thereto. The resultant reaction mixture was stirred at room temperature for about 5 hours.

When the reaction was completed, the reaction mixture was concentrated by evaporation under reduced pressure, and the residue was purified by silica gel column chromatography to obtain 1,5-di(phenylsulfonyl)-3,7,11-trimethyl-2,6,10-dodecatriene (804 mg, 1.7 mmol) (yield: 75%).

$^1$H-NMR: δ1.15 (s, 3H), 1.36 (s, 3H), 1.58 (s, 3H), 1.67 (s, 3H), 1.94 (br s, 4H), 2.33 (dd, 1H, J=13.7, 11.4 Hz), 2.93 (d, 1H, J=13.7 Hz), 3.75 (d, 2H, J=8.0 Hz), 3.86 (dt, 1H, J$_d$=2.6, J$_t$=10.4 Hz), 4.87 (d, 1H, J=10.4 Hz), 5.00 (s, 1H), 5.18 (t, 1H, J=8.0 Hz), 7.48~7.58 (m, 4H), 7.60~7.69 (m, 2H), 7.78~7.88 (m, 4H). $^{13}$C-NMR: δ16.3, 16.3, 17.7,25.7, 26.1,37.2, 39.7, 55.9, 63.0, 113.6, 116.6, 123.5, 128.3, 128.8, 129.1, 129.3, 132.0, 133.6, 133.7, 137.5, 138.8, 141.5, 146.1.

EXAMPLE 4-2

1,5-Di(phenylsulfonyl)-3,7-dimethyl-2,6-octadiene

In methyl alcohol (80 ml), dissolved was 5-phenylsulfonyl-1-phenylthio-3,7-dimethyl-2,6-octadiene (8.62 g, 22.3 mmol), and LiNbMoO$_6$ (330 mg, 1.12 mmol) and H$_2$O$_2$ (30% aqueous solution) (7.58 g, 66.9 mmol) were added thereto. The resultant reaction mixture was stirred at room temperature for about 11 hours.

When the reaction was completed, the reaction mixture was concentrated by evaporation under reduced pressure, and the residue was purified by silica gel column chromatography to obtain 1,5-di(phenylsulfonyl)-3,7-dimethyl-2,6-octadiene (8.84 g, 21.1 mmol) (yield: 95%).

$^1$H-NMR: δ1.11 (s, 3H), 1.35 (s, 3H), 1.66 (s, 3H), 2.34 (dd, 1H, J=13.8, 11.5 Hz), 2.89 (dd, 1H, J=13.8, 2.9 Hz), 3.77 (d, 2H, J=7.9 Hz), 3.85 (ddd, 1H, J=11.5, 10.4, 2.9 Hz), 4.86 (d, 1H, J=10.4 Hz), 5.16 (t, 1H, J=7.9 Hz), 7.51~7.56 (m, 4H), 7.62~7.67 (m, 2H), 7.80~7.84 (m, 4H).

$^{13}$C-NMR: δ16.2, 17.8, 25.8, 37.0, 55.8, 63.0, 113.5, 116.6, 128.2, 128.8, 129.1, 129.1, 133.6, 133.7, 137.3, 138.7, 141.3, 142.7.

EXAMPLE 5

5,9-Di(phenylsulfonyl)-1-phenylthio-3,7,11,15-tetramethyl-2,6,10,14-hexadecatetraene 1,5-Di(phenylsulfonyl)-3,7,11-trimethyl-2,6,10-dodecatriene (6.20 g, 12.7 mmol) was dissolved in THF (25 ml), and n-BuLi (1.6M solution in hexane/19 ml, 30.5 mmol) was slowly added thereto at −78° C. The resultant mixture was stirred for 30 minutes, and 4-bromo-3-methyl-2-butenyl phenyl sulfide (3.6 g, 14.0 mmol) was added to the reaction mixture. The reaction mixture was stirred at −78° C. for about 3 hours and quenched with 1M-HCl solution (20 ml).

The mixture was slowly warmed up to room temperature and extracted with ether (100 ml). The ether extract was subsequently washed with distilled water (30 ml), dried over anhydrous sodium sulfate, and filtered.

The filtrate was concentrated by evaporation under reduced pressure, and the residue was purified by silica gel column chromatography to obtain 5,9-di(phenylsulfonyl)-1-phenylthio-3,7,11,15-tetramethyl-2,6,10,14-hexadecatetraene (7.66 g, 11.6 mmol) (yield: 91%).

$^1$H-NMR: δ1.16 (d, 3H, J=1.1 Hz), 1.35 (s, 3H), 1.47 (s, 3H), 1.58 (s, 3H), 1.67 (s, 3H), 1.94 (br s, 4H), 2.14 (dd, 1H, J=13.2, 11.9 Hz), 2.26 (dd, 1H, J=13.6, 11.5 Hz), 2.73 (d, 1H, J=13.0 Hz), 2.91 (d, 1H, J=12.8 Hz), 3.44 (d, 2H, J=7.8 Hz), 3.72~3.94 (m, 2H), 4.85 (d, 1H, J 9.3 Hz), 4.92 (d, 1H, J=9.6 Hz), 5.02 (br s, 1H), 5.24 (t, 1H, J=7.8 Hz), 7.14~7.33 (m, 5H), 7.40~7.55 (m, 4H), 7.55~7.67 (m, 2H), 7.70~7.87 (m, 4H).

$^{13}$C-NMR: δ15.9, 16.5, 17.0, 17.7, 25.7, 26.1, 31.7, 37.3, 38.1, 39.9, 62.9, 63.4, 117.0, 119.7, 123.2, 123.6, 126.2, 128.7, 128.8, 128.9, 129.0, 129.3, 129.5, 131.9, 133.5, 133.7, 134.2, 136.3, 137.4, 137.5, 141.2, 145.9.

EXAMPLE 6

1,5,9-Tri(phenylsulfonyl)-3,7,11,15-tetramethyl-2,6,10,14-hexadecatetraene

In methyl alcohol (50 ml), dissolved was 5,9-di(phenylsulfonyl)-1-phenylthio-3,7,11,15-tetramethyl-2,6,10,14-hexadecatetrane (7.03 g, 10.6 mmol), and LiNbMoO$_6$ (77 mg, 0.27 mmol) and H$_2$O$_2$ (30% aqueous solution) (3.61 g, 31.8 mmol) were added thereto. The resultant reaction mixture was stirred at room temperature for about 5 hours.

When the reaction was completed, the reaction mixture was diluted with CHCl$_3$ (100 ml), washed with distilled water (30 ml), dried over anhydrous sodium sulfate, and filtered. The filtrate was concentrated by evaporation under reduced pressure, and the residue was purified by silica gel column chromatography to obtain 1,5,9-tri(phenylsulfonyl)-3,7,11,15-tetramethyl-2,6,10,14-hexadecatetraene (5.33 g, 7.7 mmol) (yield: 72%).

$^1$H-NMR: δ1.14 (d, 3H, J=1.2 Hz), 1.32 (s, 3H), 1.34 (d, 3H, J=1.1 Hz), 1.58 (s, 3H), 1.67 (s, 3H), 1.92 (br s, 4H), 2.15~2.36 (m, 2H), 2.70~2.98 (m, 2H), 3.72 (d, 2H, J=7.8 Hz), 3.83 (ddd, 1H, J=10.9, 10.9, 3.2 Hz), 3.91 (ddd, 1H, J=10.3, 10.3, 3.3 Hz), 4.89 (d, 1H, J=10.3 Hz), 4.93 (d, 1H, J=10.9 Hz), 5.02 (br s, 1H), 5.12 (t, 1H, J=7.8 Hz), 7.40~7.71 (m, 9H), 7.71~7.93 (m, 6H). $^{13}$C-NMR: δ16.1, 16.4, 16.7, 17.6, 25.6, 26.0, 37.6, 38.1, 39.8, 55.7, 62.6, 63.0, 113.7, 117.1, 119.4, 123.6, 128.1, 128.7, 128.9, 128.9. 129.1, 129.2, 131.8, 133.5, 133.7, 133.7, 137.3, 137.4, 138.8, 140.9, 141.7, 145.8.

EXAMPLE 7-1

Di(5,9-di(phenylsulfonyl)-3,7,11,15-tetramethyl-2,6,10,14-hexadecatetaenyl) sulfide In THF (50 ml), dissolved was 1,5-di(phenylsulfonyl)-3,7,11-trimethyl-2,6,10-dodecatriene (9.00 g, 18.5 mmol). To the solution, n-BuLi (1.6M solution in hexane/23 ml, 37 mmol) was slowly added thereto at −78° C. The resultant mixture was stirred for 20 minutes, and di(4-bromo-3-methyl-2-butenyl sulfide (E) (3.03 g, 9.2 mmol) was added to the reaction mixture. After stirring the mixture at the same temperature for 3 hours, aqueous 1M-HCl solution (10 ml) was added thereto to quench the reaction.

The temperature of the reaction mixture was slowly raised to room temperature, and ether (100 ml) was added. The resultant mixture was subsequently washed with aqueous 1M-HCl solution (20 ml×2) and distilled water (30 ml). The mixture was dried over anhydrous sodium sulfate, and filtered.

The filtrate was concentrated by evaporation under reduced pressure, and the residue was purified by silica gel column chromatography to obtain di(5,9-di(phenylsulfonyl)-3,7,11,15-tetramethyl-2,6,10,14-hexadecatetraenyl) sulfide (9.39 g, 8.2 mmol) (yield: 89%).

$^1$H-NMR: δ1.16 (s, 6H), 1.41 (s, 6H), 1.49 (s, 6H), 1.58 (s, 6H), 1.68 (s, 6H), 1.95 (br s, 8H), 2.15 (dd, 2H, J=13.0, 11.9 Hz), 2.30 (dd, 2H, J=12.6, 11.0 Hz), 2.73 (d, 2H, J=13.0 Hz), 2.86 (d, 2H, J=12.6 Hz), 2.95 (d, 4H, J=7.0 Hz), 3.86 (m, 4H), 4.87 (d, 2H, J=10.6 Hz), 4.93 (d, 2H, J=9.9 Hz), 5.02 (br s, 2H), 5.18 (t, 2H, J 7.0 Hz), 7.46~7.58 (m, 8H), 7.58~7.69 (m, 4H), 7.72~7.90 (m, 8H). $^{13}$C-NMR: δ15.8, 16.4, 16.8, 17.6, 25.6, 26.0, 28.6, 37.3, 38.4, 39.8, 62.9, 63.2, 116.8, 119.8, 123.5, 124.3, 128.7, 128.8, 129.0, 129.2, 131.9, 133.2, 133.5, 133.6, 137.4, 137.5, 141.1, 146.0.

EXAMPLE 7-2

Di(5,9-di(phenylsulfonyl)-3,7,11-trimethyl-2,6,10-dodecatrienyl) sulfide

In THF (50 ml), dissolved was 1,5-di(phenylsulfonyl)-3,7-dimethyl-2,6-octadiene (4.61 g, 11.0 mmol). To the solution, n-BuLi (1.6M solution in hexane/16.5 ml, 26.4 mmol) was slowly added thereto at −78° C. The resultant mixture was stirred for 20 minutes, and di(4-bromo-3-methyl-2-butenyl) sulfide (E) (1.75 g, 5.33 mmol) was added to the reaction mixture. After stirring the mixture at the same temperature for 3 hours, aqueous 1M-HCl solution (10 ml) was added thereto to quench the reaction.

The temperature of the reaction mixture was slowly raised to room temperature, and ether (100 ml) was added. The resultant mixture was subsequently washed with aqueous 1M-HCl solution (20 ml×2) and distilled water (30 ml). The mixture was dried over anhydrous sodium sulfate, and filtered.

The filtrate was concentrated by evaporation under reduced pressure, and the residue was purified by silica gel column chromatography to obtain di(5,9-di(phenylsulfonyl)-3,7,11-trimethyl-2,6,10-dodecatrienyl) sulfide (4.80 g, 4.79 mmol) (yield: 87%).

$^1$H-NMR: δ1.12 (s, 6H), 1.42 (s, 6H), 1.49 (s, 6H), 1.69 (s, 6H), 2.03~2.38 (m, 4H), 2.65~3.20 (m, 8H), 3.88 (m, 4H), 4.82 (d, 2H, J=10.2 Hz), 4.91 (d, 2H, J=9.9 Hz), 5.12 (t, 2H, J=7.3 Hz), 7.53~7.65 (m, 12H), 7.76~7.84 (m, 8H). $^{13}$C-NMR: δ15.8, 16.8, 17.9, 25.9, 28.5, 37.1, 38.4, 62.8, 63.1, 116.9, 119.6, 124.4, 128.8, 128.8, 128.9, 129.1, 133.7, 136.7, 137.1, 137.2, 140.4, 140.9, 142.7.

EXAMPLE 8-1

Di(5,9-di(phenylsulfonyl)-3,7,11,15-tetramethyl-2,6,10,14-hexadecatetaenyl) sulfone In methyl alcohol (20 ml), dissolved was di(5,9-di(phenylsulfonyl)-3,7,11,15-tetramethyl-2,6,10,14- hexadecatetraenyl sulfide (2.0 g, 1.75 mmol), and LiNbMoO$_6$ (26 mg, 0.09 mmol) and H$_2$O$_2$ (30% aqueous solution) (0.99 g, 8.75 mmol) were added thereto. The resultant reaction mixture was stirred at room temperature for about 5 hours.

When the reaction was completed, the reaction mixture was concentrated by evaporation under reduced pressure, and the residue was purified by silica gel column chromatography to obtain Di(5,9-di(phenylsulfonyl)-3,7,11,15-tetramethyl-2,6,10,14-hexadecatetraenyl) sulfone (1.48 g, 1.26 mmol) (yield: 72%).

$^1$H-NMR: δ1.15 (s, 6H), 1.41 (s, 6H), 1.58 (s, 6H), 1.61 (s, 6H), 1.67 (s, 6H), 1.93 (br s, 8H), 2.17~2.37 (m, 4H), 2.81 (d, 2H, J=12.3 Hz), 2.91 (d, 2H, J=14.1 Hz), 3.56 (d, 4H, J=7.2 Hz), 3.91 (dt, 4H, J$_d$=2.8, J$_t$=9.6 4.89 (d, 2H, J=8.8 Hz), 4.92 (d, 2H, J=10.1 Hz), 5.01 (br s, 2H), 5.23 (t, 2H J=7.2 Hz), 7.47~7.58 (m, 8H), 7.58~7.67 (m, 4H), 7.74~7.89 (m, 8H). $^{13}$C-NMR: δ16.4, 16.5, 16.6, 17.6, 25.6, 26.0, 37.7, 38.4, 39.7, 51.6, 62.5, 62.8, 113.7, 116.9, 118.5, 123.6, 128.7, 128.9, 128.9, 129.2, 131.7, 133.5, 133.7, 137.2, 140.8, 140.9, 141.6, 145.8.

EXAMPLE 8-2

Di(5,9-di(phenylsulfonyl)-3,7,11-trimethyl-2,6,10-dodecatrienyl) sulfone

In methyl alcohol (50 ml), dissolved was di(5,9-di(phenylsulfonyl)-3,7,11-trimethyl-2,6,10-dodecatrienyl) sulfide (4.54 g, 4.52 mmol), and LiNbMoO$_6$ (66 mg, 0.23 mmol) and H$_2$O$_2$ (30% aqueous solution) (1.54 g, 13.6 mmol) were added thereto. The resultant reaction mixture was stirred at room temperature for about 6 hours.

When the reaction was completed, the reaction mixture was concentrated by evaporation under reduced pressure, and the residue was purified by silica gel column chromatography to obtain Di(5,9-di(phenylsulfonyl)-3,7,11-trimethyl-2,6,10-dodecatrienyl) sulfone (3.28 g, 3.16 mmol) (yield: 70%).

$^1$H-NMR: δ1.05 (s, 6H), 1.41 (s, 6H), 1.61 (s, 6H), 1.67 (s, 6H), 2.17~2.47 (m, 4H), 2.74~2.99 (m, 4H), 3.57 (br s, 4H), 3.79~4.02 (m, 4H), 4.86 (d, 2H, J=9.9 Hz), 4.90 (d, 2H, J=10.8 Hz), 5.21 (t, 2H, J=7.5 Hz), 7.51~7.55 (m, 8H), 7.61~7.66 (m, 4H), 7.76~7.82 (m, 8H). $^{13}$C-NMR: δ16.6, 16.7, 17.9, 25.9, 37.5, 38.7, 51.6, 62.6, 62.8, 113.7, 117.1, 119.4, 128.8, 129.0, 129.0, 129.2, 133.6, 133.8, 137.1, 141.0, 141.0, 141.6, 142.7.

EXAMPLE 9-1

7,7',11,11'-Tetra(phenylsulfonyl)-7,7',8,8',11,11', 12,12'-octahydrolycopene

Di(5,9-di(phenylsulfonyl)-3,7,11,15-tetramethyl-2,6,10,14-hexadecatetraenyl)sulfone (1.10 g, 0.94 mmol) was dissolved in a mixture of t-butanol (30 ml) and CCl$_4$ (30 ml). Minutely pulverized KOH (1.68 g, 30.0 mmol) was added thereto under argon atmosphere at room temperature. The reaction mixture was vigorously stirred for 5 hours.

When the reaction was completed, methylene chloride (60 ml) was added thereto to dissolve the mixture, and the resultant solution was washed with 1M-HCl (20 ml). The combined methylene chloride layer was dried over anhydrous sodium sulfate, and filtered. The filtrate was concentrated by evaporation under reduced pressure, and the residue was purified by silica gel column chromatography to obtain 7,7',11,11'-tetra(phenylsulfonyl)-7,7',8,8',11,11',12,12'-octahydrolycopene (822 mg, 0.74 mmol) (yield: 79%).

$^1$H-NMR: δ1.14 (br s, 6H), 1.33 (s, 6H), 1.58 (s, 6H), 1.60 (s, 6H), 1.67 (s, 6H), 1.93 (br s, 8H), 2.16~2.42 (m, 4H), 2.63~3.07 (m, 4H), 3.68~4.05 (m, 4H), 4.91 (d, 4H, J=10.6 Hz), 4.98 (br s, 2H), 5.69~5.90 (br s, 2H), 6.08~6.24 (m, 2H), 7.45~7.58 (m, 8H), 7.58~7.70 (m, 4H), 7.73~7.87 (m, 8H). $^{13}$C-NMR: δ16.4, 17.1, 17.7, 24.9, 25.6, 26.1, 28.5, 37.9, 39.8, 63.0, 63.6, 116.6, 116.8, 119.9, 123.5, 127.8, 128.7, 128.8, 129.0, 129.1, 129.2, 132.0, 133.6, 137.5, 140.6, 141.4, 145.9, 146.1.

EXAMPLE 9-2

2,6,10,15,19,23-Hexamethyl-4,8,17,21-tetra (phenylsulfonyl)-2,6,10,12,14,18,22-tetraeicosaheptaene Di(5,9-di(phenylsulfonyl)-3,7,11-trimethyl-2,6,10-dodecatrienyl) sulfone (1.17 g, 1.13 mmol) was dissolved in a mixture of t-butanol (30 ml) and CCl$_4$ (30 ml). Minutely pulverized potassium hydroxide (KOH/1.90 g, 33.8 mmol) was added thereto under argon atmosphere at room temperature. The reaction mixture was vigorously stirred for 7 hours.

When the reaction was completed, methylene chloride (70 ml) was added thereto to dissolve the mixture, and the resultant solution was washed with 1M-HCl (20 ml). The combined methylene chloride layer was dried over anhydrous sodium sulfate, and filtered. The filtrate was concentrated by evaporation under reduced pressure, and the residue was purified by silica gel column chromatography to obtain 2,6,10,15,19,23-hexamethyl-4,8,17,21-tetra (phenylsulfonyl)-2,6,10,12,14,18,22-tetraeicosaheptaene (839 mg, 0.87 mmol) (yield: 77%).

$^1$H-NMR: δ1.06 (s, 6H), 1.57 (br s, 6H), 1.61 (s, 6H), 1.66 (s, 6H), 2.12~2.52 (m, 4H), 2.68~3.07 (m, 4H), 3.64~4.04 (m, 4H), 4.65~5.03 (m, 4H), 5.69~5.91 (br d, 2H, J=18.5 Hz), 6.08~6.26 (m, 2H), 7.43~7.59 (m, 8H), 7.59~7.70 (m, 4H), 7.73~7.87 (m, 8H).

EXAMPLE 10-1

Lycopene

In a mixture of ethanol (20 ml) and benzene (5 ml), dissolved was 7,7',11,11'-tetra(phenylsulfonyl)-7,7',8,8',11,11',12,12'-octahydrolycopene (H-1) (682 mg, 0.62 mmol). Sodium ethoxide (NaOEt) (3.35 g, 49.3 mmol) was added thereto under argon atmosphere.

The reaction mixture was heated under reflux with vigorous stirring for 12 hours.

When the reaction was completed, benzene (50 ml) was added thereto to dissolve the mixture, and the resultant solution was washed with 1M-HCl (10 ml). The combined organic layer was dried over anhydrous sodium sulfate, and filtered. The filtrate was concentrated by evaporation under reduced pressure, and the residue was purified by silica gel column chromatography to obtain lycopene of Chemical Formula 2 (260 mg, 0.48 mmol) (yield: 78%).

$^1$H-NMR: δ1.61 (s, 6H), 1.68 (s, 6H), 1.82 (s, 6H), 1.96 (s, 12H), 2.11 (br s, 8H), 5.11 (br s, 2H), 5.95 (d, 2H, J=10.8 Hz), 6.18 (d, 2H, J=12.1 Hz), 6.24 (d, 2H, J=14.9 Hz), 6.20~6.30 (m, 2H), 6.35 (d, 2H, J=14.8 Hz), 6.49 (dd, 2H, J=14.9, 10.8 Hz), 6.63 (dd, 2H, J=14.8, 12.1 Hz), 6.55~6.70 (m, 2H). $^{13}$C-NMR: δ12.8, 12.9, 17.0, 17.7, 25.7, 26.7, 40.2, 123.9, 124.8, 125.1, 125.7, 130.1, 131.5, 131.8, 132.6, 135.4, 136.2, 136.5, 137.3, 139.5.

The analytical data of lycopene as above corresponds to NMR data of trans-lycopene as previously reported (*Helv. Chim. Acta* 1992, 75, 1848–1865).

EXAMPLE 10-2

2,6,10,15,19,23-Hexamethyl-2,4,6,8,10,12,14,16,18,20,22-tetraeicosaundecaene In a mixture of ethanol (30 ml) and benzene (5 ml), dissolved was 2,6,10,15,19,23-hexamethyl-4,8,17,21-tetra (phenylsulfonyl)-2,6,10,12,14,18,22-tetraeicosaheptaene (730 mg, 0.75 mmol). Sodium ethoxide (NaOEt) (4.10 g, 60 3 mmol) was added thereto under argon atmosphere.

The reaction mixture was heated under reflux with vigorous stirring for 12 hours. Then the reaction was completed, benzene (60 ml) was added thereto to dissolve the mixture, and the resultant solution was washed with 1M-HCl (10 ml). The combined organic layer was dried over anhydrous sodium sulfate, and filtered. The filtrate was concentrated by evaporation under reduced pressure, and the residue was purified by silica gel column chromatography to obtain 2,6,10,15,19,23-hexamethyl-2,4,6,8,10,12,14,16,18,20,22-tetraeicosaundecaene (213 mg, 0.53 mmol) (yield: 71%).

$^1$H-NMR: δ1.82 (s, 12H), 1.97 (s, 12H), 5.94 (d, 2H, J=11 Hz), 6.18 (d, 2H,J=12.7 Hz), 6.22 (d, 2H, J=15.3 Hz), 6.16~6.31 (m, 2H), 6.35 (d, 2H, J=14.8 Hz), 6.48 (dd, 2H, J=15.3, 11 Hz), 6.63 (dd, 2H, J=14.8, 12.7 Hz), 6.54~6.67 (m, 2H).

What is claimed is:

1. An allylic sulfide represented by following Chemical Formula 1:

Chemical formula 1

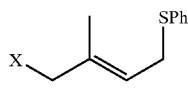

wherein, X is selected from the group consisting of —Cl, —Br, —I, —OSO$_2$CF$_3$, —OSO$_2$Ph, —OSO$_2$C$_6$H$_4$CH$_3$ and —OSO$_2$CH$_3$, and Ph represents phenyl group.

2. A process for preparing an allylic sulfide of Chemical Formula 1, which comprises the steps of (a-1) oxidizing isoprene to obtain isoprene monoxide; (b-1) reacting the isoprene monoxide with benzenethiol to obtain 4-hydroxy-3-methyl-2-butenyl phenyl sulfide (A); and (c-1) reacting the compound (A) with a halogenating compound or sulfonylating compound.

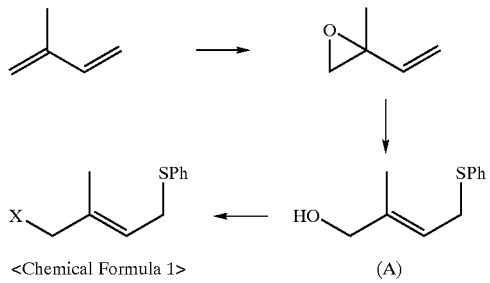

in the formulas, X is selected from the group consisting of —Cl, —Br, —I, —OSO$_2$CF$_3$, —OSO$_2$Ph, —OSO$_2$C$_6$H$_4$CH$_3$ and —OSO$_2$CH$_3$, and Ph represents phenyl group.

3. A process according to claim 2, Cu(I)-containing salt is used as the catalyst and N,N-dimethylformamide (DMF) as the solvent in stage (b-1).

4. A process according to claim 3, wherein the Cu(I)-containing salt is one or more salt(s) selected from the group consisting of CuCN, CuI, CuBr and CuCl.

5. A process for extending carbon chain by the use of allylic sulfide of Chemical Formula 1, which comprises the steps of (a-2) deprotonating allylic sulfone compound (B), and reacting the resultant compound with allylic sulfide of Chemical Formula 1 to obtain thio-sulfone compound (C); and (b-2) selectively oxidizing the thio-sulfone compound (C) to obtain the corresponding allylic sulfone compound (D).

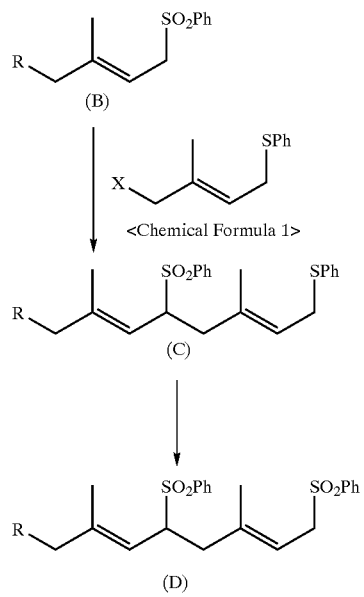

in the formulas, R is selected from the group consisting of hydrogen, C1~C30 alkyl group, C1~C30 alkenyl group, aryl group, —CN, —COOR' (wherein, R' is C1~C10 alkyl group) and —C(═O)H, X is selected from the group consisting of —Cl, —Br, —I, —OSO$_2$CF$_3$, —OSO$_2$Ph, —OSO$_2$C$_6$H$_4$CH$_3$ and —OSO$_2$CH$_3$, and Ph represents phenyl group.

6. A process according to claim 5, wherein C-5 unit is added by repeating stages (a-2) and (b-2) one or more times by using compound (D) as the starting material.

7. A process according to claim 5, wherein stage (b-2) is performed by adding hydrogen peroxide solution dropwise to the sulfide compound (C) in the presence of lithium molybdenate-niobate (LiNbMoO$_6$) or vanadium oxide (V$_2$O$_5$) as a catalyst.

8. A process for preparing a carotenoid polyene chain compound represented by Chemical formula 2, which comprises the steps of (a-3) deprotonating the allylic disulfone compound (D), and reacting the resultant compound with not more than 0.5 equivalent of diallylic sulfide (E) (wherein, Y is a halogen atom) on the basis of 1 equivalent of allylic disulfone compound (D) to obtain allylic sulfide compound (F); (b-3) selectively oxidizing the allylic sulfide compound (F) to obtain allylic sulfone compound (G); (c-3) subjecting the allylic sulfone compound (G) to Ramberg-Bäklund reaction to give tetra(phenylsulfonyl)-triene compound (H); and (d-3) reacting the compound (H) with a base.

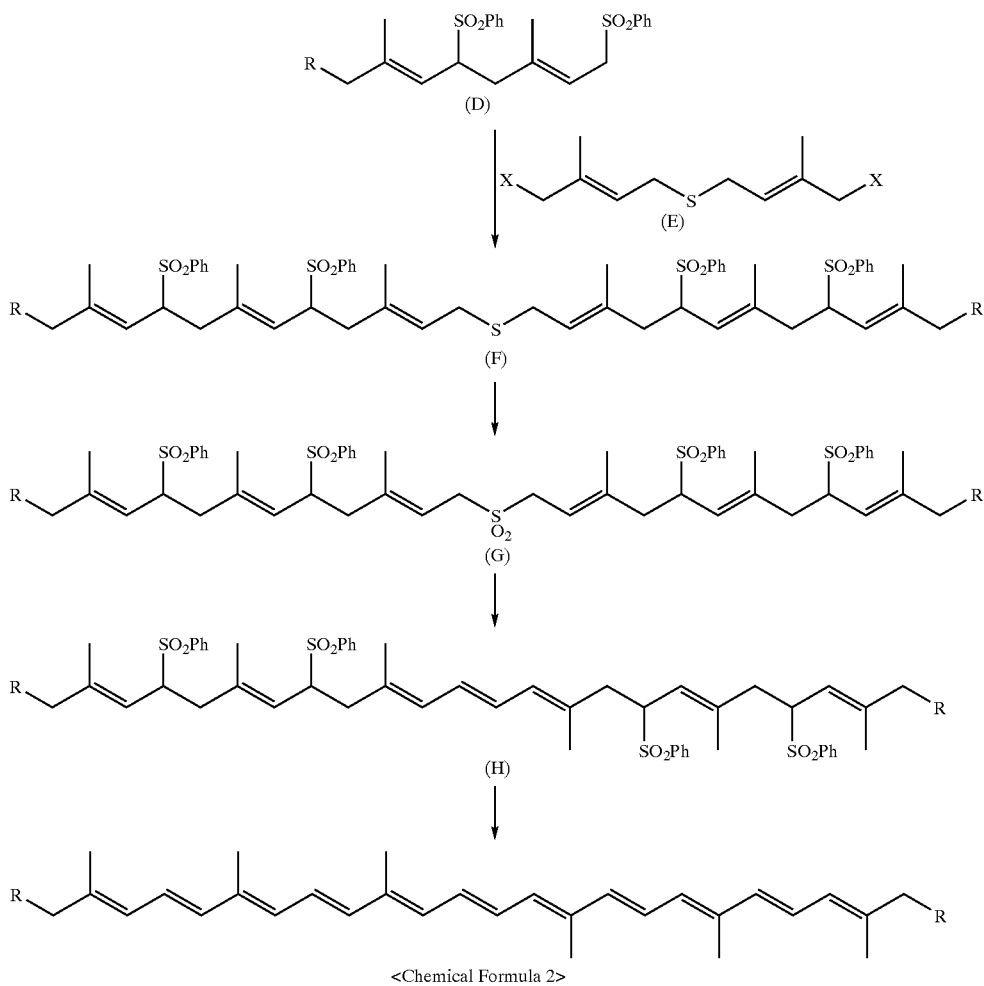

<Chemical Formula 2> in the formulas, R is selected from the group consisting of hydrogen, C1~C30 alkyl group, C1~C30 alkenyl group, aryl group, —CN, —COOR' (wherein, R' is C1~C10 alkyl group) and —C(=O)H, Y is selected from the group consisting of —Cl, —Br, —I, —OSO$_2$CF$_3$, —OSO$_2$Ph, —OSO$_2$C$_6$H$_4$CH$_3$ and —OSO$_2$CH$_3$, and Ph represents phenyl group.

9. A process according to claim 8, wherein R represents hydrogen or prenyl.

10. A process according to claim 8, wherein the deprotonation step of disulfone compound (D) in stage (a-3) is performed by adding not less than 2 equivalent of base dropwise to 1 equivalent of allylic disulfone compound (D) at a temperature of −40° C. or lower.

11. A process according to claim 8, wherein stage (b-3) is performed by adding a mixture of urea-hydrogen peroxide (UHP) and phthalic anhydride to allylic sulfide compound (F) at a low temperature, or by adding hydrogen peroxide (H$_2$O$_2$) solution in the presence of LiNbMoO$_6$ or V$_2$O$_5$ as a catalyst at ambient temperature.

12. A process according to claim 8, wherein Ramberg-Baklund reaction of stage (c-3) is carried out under nitrogen or argon atmosphere.

13. A process according to claim 8, wherein the base used at stage (d-3) is a metal alkoxide.

14. A process according to claim 9, wherein the deprotonation step of disulfone compound (D) in stage (a-3) is performed by adding not less than 2 equivalent of base dropwise to 1 equivalent of allylic disulfone compound (D) at a temperature of −40° C. or lower.

15. A process according to claim 9, wherein stage (b-3) is performed by adding a mixture of urea-hydrogen peroxide (UHP) and phthalic anhydride to allylic sulfide compound (F) at a low temperature, or by adding hydrogen peroxide (H$_2$O$_2$) solution in the presence of LiNbMoO$_6$ or V$_2$O$_5$ as a catalyst at ambient temperature.

16. A process according to claim 9, wherein Ramberg-Baklund reaction of stage (c-3) is carried out under nitrogen or argon atmosphere.

17. A process according to claim 9, wherein the base used at stage (d-3) is a metal alkoxide.

18. An allylic sulfone represented by the following compound (D):

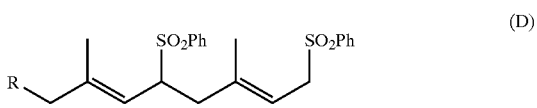

wherein R is selected from the group consisting of hydrogen, C$_1$–C$_6$ alkyl group, C$_1$–C$_6$ alkenyl group, and aryl group, and Ph represents phenyl group.

* * * * *